(12) United States Patent
Manganini et al.

(10) Patent No.: US 6,803,237 B2
(45) Date of Patent: Oct. 12, 2004

(54) SEQUENTIAL PROCESSING REACTION VESSEL FOR CHEMICAL FRACTIONATION AND ANALYSIS

(75) Inventors: Steven J. Manganini, Falmouth, MA (US); Kenneth W. Doherty, Falmouth, MA (US); Terence R. Hammer, East Falmouth, MA (US); Bruce A. Lancaster, Waquoit, MA (US)

(73) Assignee: Woods Hole Oceanographic Institution, Woods Hole, MA (US)

( * ) Notice: Subject to any disclaimer, the term of this patent is extended or adjusted under 35 U.S.C. 154(b) by 512 days.

(21) Appl. No.: 09/771,354

(22) Filed: Jan. 25, 2001

(65) Prior Publication Data

US 2003/0031600 A1 Feb. 13, 2003

Related U.S. Application Data

(60) Provisional application No. 60/177,837, filed on Jan. 25, 2000.

(51) Int. Cl.[7] .................... G01N 1/44; G05D 23/00; B01L 3/00

(52) U.S. Cl. .............. 436/175; 219/710; 219/712; 219/762; 422/68.1; 422/78; 422/99; 422/101; 422/102; 422/104; 422/109; 436/55; 436/60; 436/155; 436/157; 436/159; 436/177; 436/182; 436/183

(58) Field of Search ........................ 436/55, 60, 155, 436/157, 159, 175, 177, 181–183; 422/68.1, 78, 99–102, 104, 109, 288, 307; 219/697, 710, 712, 756, 757, 762

(56) References Cited

U.S. PATENT DOCUMENTS

| 4,613,738 A | 9/1986 | Saville |
| 4,670,404 A | 6/1987 | Swift et al. |
| 4,736,083 A | 4/1988 | Saville |
| 4,877,624 A | 10/1989 | Floyd et al. |
| 4,882,128 A | 11/1989 | Hukvari et al. |
| 4,904,450 A | 2/1990 | Floyd |
| 4,933,529 A | 6/1990 | Saville |

(List continued on next page.)

FOREIGN PATENT DOCUMENTS

JP 5-305202 * 11/1993

OTHER PUBLICATIONS

Mohd, A. A. et al, Analyst 1992, 117, 1743–1748.*
Totland, M. M. et al, Chemical Geology 1995, 124, 21–36.*
Wang, C.–F. et al, Analytica Chimica Acta 1996, 320, 207–216.*

(List continued on next page.)

Primary Examiner—Arlen Soderquist
(74) Attorney, Agent, or Firm—R. Dennis Creehan, Esq.

(57) ABSTRACT

A sequential processing reactor vessel and method is disclosed for accelerated extraction and fractionation of chemical analytes from complex solid sample materials. The device and method provide for sequential extraction of elemental constituents from solid materials by sequentially contacting target samples within a single reaction vessel using a series of different reagents at temperatures as high as 150° C. and pressures up to 150 psi to accelerate reactions. The aggressive chemical treatments provided by the disclosed device and method enable the complete digestion of solid samples in liquid analyte samples that can be directly analyzed by conventional spectrometry or other suitable methods. The disclosed device and method provide for efficient sample processing and accelerated reactions to significantly reduce processing times and costs for elemental analysis of solids while improving accuracy, precision and reliability of results compared to conventional devices and methods. The disclosed device and method are compatible with both conventional convection and radiant heating sources as well as microwave heating and can be readily adapted to marine, geological, environmental, industrial and research solids analysis applications.

23 Claims, 9 Drawing Sheets

U.S. PATENT DOCUMENTS

| | | |
|---|---|---|
| 4,963,261 A | 10/1990 | Witkowski et al. |
| 5,013,522 A | 5/1991 | Granath et al. |
| 5,204,065 A | 4/1993 | Floyd |
| 5,264,185 A | 11/1993 | Floyd |
| 5,369,034 A | 11/1994 | Hargett et al. |
| 5,382,414 A | 1/1995 | Lautenschlager |
| 5,647,976 A | 7/1997 | Rothe et al. |
| 5,948,307 A | 9/1999 | Stalling |

OTHER PUBLICATIONS

Wu, S. et al, Journal of Analytical Atomic Spectrometry 1996, 11, 287–296.*

Kingston, H. M. et al, Analytical Chemistry 1986, 58, 2534–2541.*

Matusiewicz, H. Journal of Analytical Atomic Spectrometry 1991, 6, 283–287.*

Karanassios, V. et al, Journal of Analytical Atomic Spectrometry 1991, 6, 457–463.*

Kojima, I. et al, Analytica Chimica Acta 1992, 264, 101–106.*

Zhi, Z.-L. et al, Critical Reviews in Analytical Chemistry 1996, 26, 239–260.*

Beary, E. S. et al, Analytical Chemistry 1997, 69, 758–766.*

Robbat, A., Jr. et al, Fresenius' Journal of Analytical Chemistry 1999, 364, 305–312.*

Hassler, D. R. et al, Chemical Geology 2000, 166, 1–14.*

Anonymous, "Operation Manual: Microwave Sample Preparation System MDS–2100," CEM Corp. (Matthews, NC) 1994, pp. 29–30 & 49–51.

Anonymous, "Laboratory Catalogue 2000–2001," Millipore Corp. (Bedford, MA), 2000, pp. 29–30, 203 & 213.

Anonymous, "ASE 200 Accelerated Solvent Extractor Operator's Manual," Dionex Corp. (Sunnyvale, CA) 1997, pp. 2–1, 2–10, 3–5, 3–6 and 5–2.

Anonymous, "The Filter Book," Pall Gelman Laboratory (Ann Arbor, MI) 1998, p. 48.

Anonymous, "Poretics Products Catalog: Microfiltration and Laboratory Products, 1997–1998 Edition," Osmotics Inc. (Minnetonka, MN) 1997, one page.

Anonymous, "ISM Supported Membranes," Interflo Innovation News, Chromex Corp. (Brooklyn, NY) Date unknown, 2 pages.

Anonymous, "Teflon PFA Molded Products for Science and Industry," Savillex Corp. (Minnetonka, MN) 1994, multiple pages.

* cited by examiner

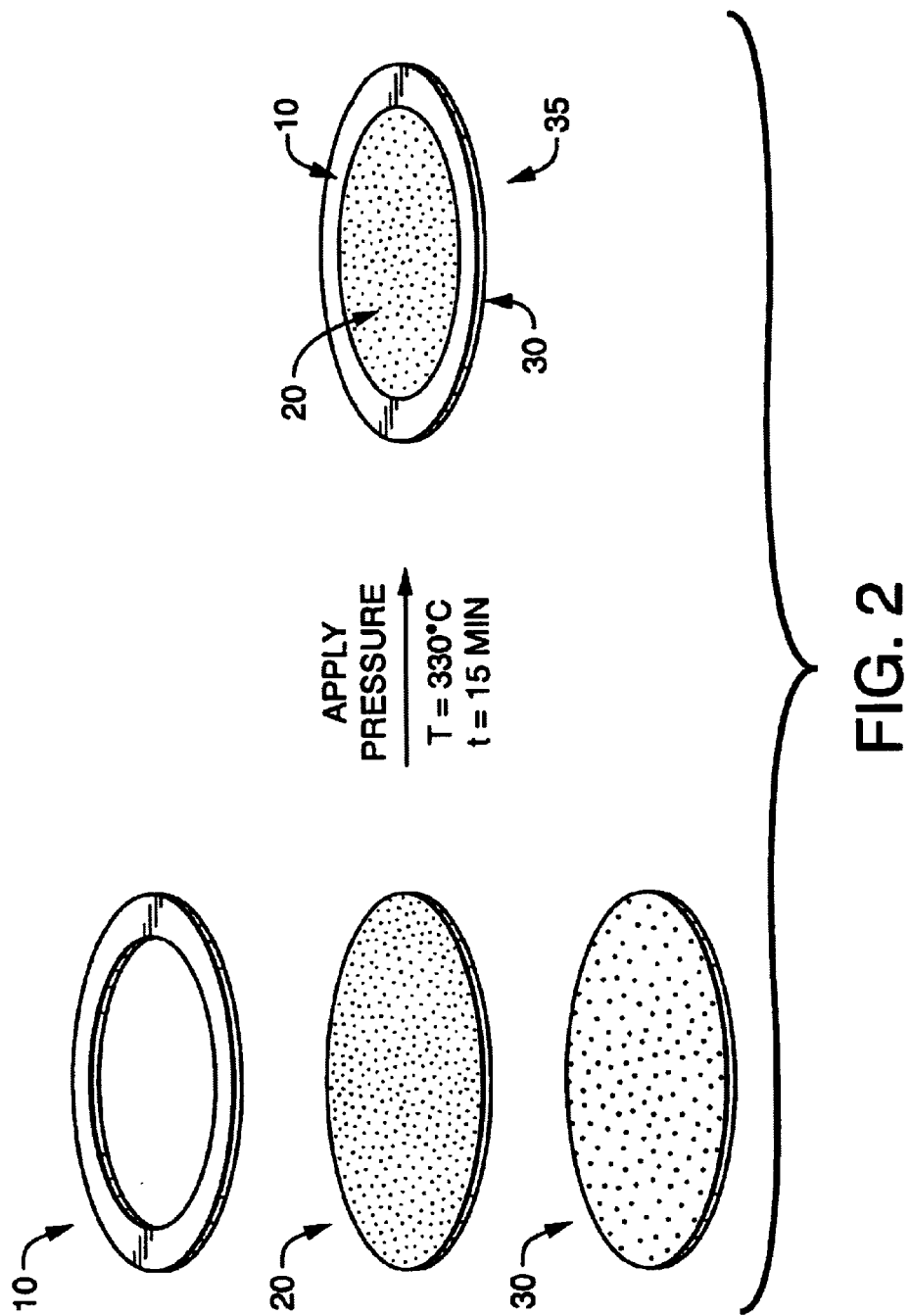

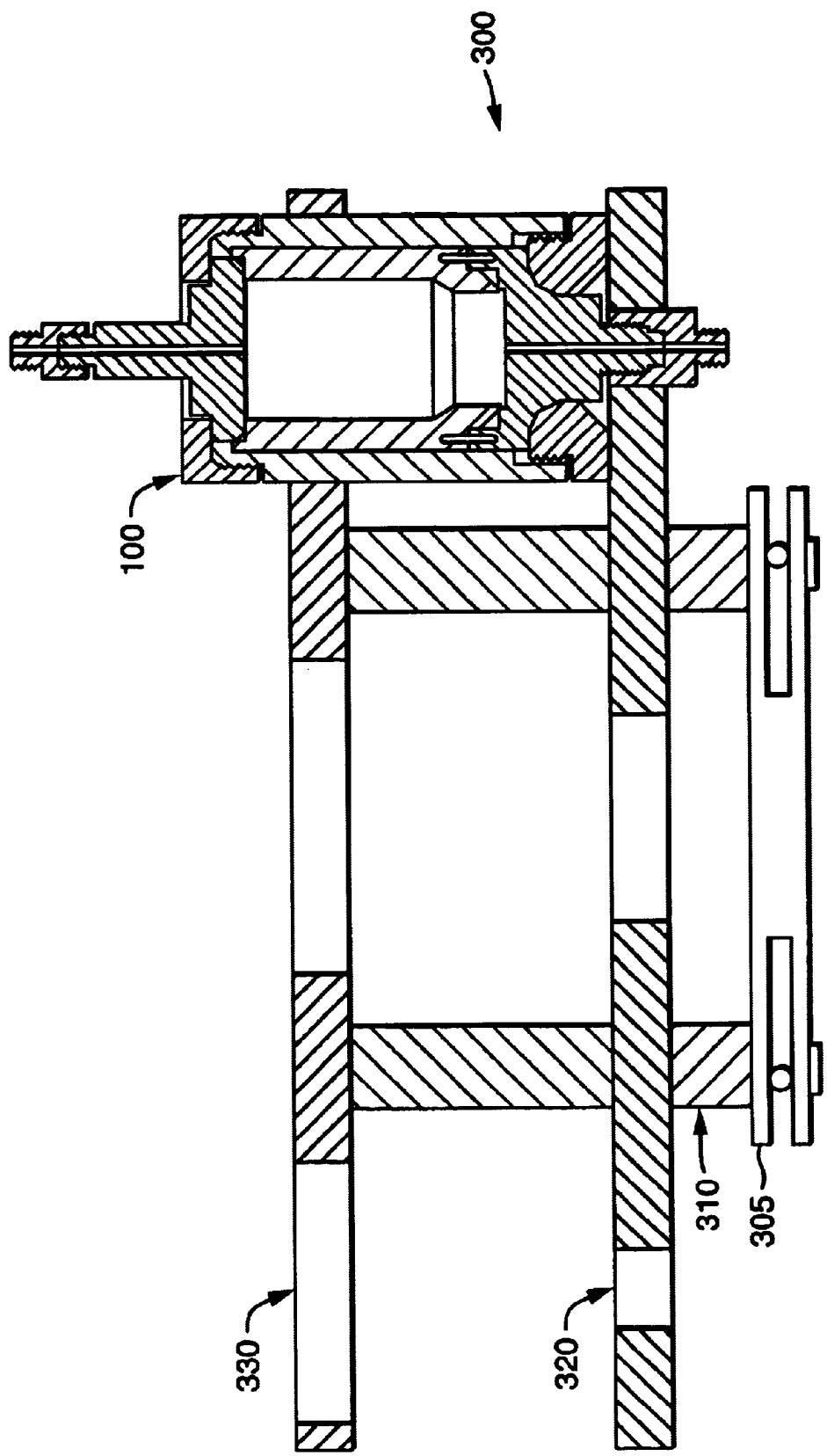

SEQUENTIAL PROCESSING REACTION VESSEL FOR CHEMICAL FRACTIONATION AND ANALYSIS

CROSS-REFERENCES

This application is U.S. provisional patent application U.S. Ser. No. 60/177,837 filed on Jan. 25, 2000 which is incorporated herein by this reference. A

FIELD OF THE INVENTION

This invention relates to devices and methods for sequential fractionation and extract of elements from complex solid samples. More particularly, this invention relates to a sequential processing reaction vessel and method for accelerated fractionation and extraction of analytes from solid samples which is compatible with microwave heating sources and which reduces processing time and transfer losses, improves extraction efficiency, and provides for accurate total analysis of solid samples.

BACKGROUND OF THE INVENTION

Sequential extraction methods have been previously developed to address specific questions to enhance understanding of elemental behavior in complex oceanographic and geological samples [see R. Chester et al., *Chemical Geology*, 2: 249–262 (1967); A. Tessler et al., *Analytical Chemistry*, 51(7): 844–850 (1979); D. W. Eggimann et al., *Jour. Sediment Petrol.* 50: 215–225 (1980); J. M. Robbins et al., "A Sequential Extraction Procedure for partitioning elements among co-existing phases in marine sediments", College of Oceanography, Oregon State University, Ref.#84-3, 64pp. (1984); S. B. Moran et al., *Geochimica Cosmochimica Acta*, 55: 2745–2751 (1991); and R. Chester et al., *Journal of the Geological Society, London*, 151: 351–360 (1994)].

Analytical techniques most commonly used for the chemical fractionation of Si in biogenic and lithogenic sedimentary particles are based on the higher solubility of biogenic silica in alkaline solutions at elevated temperature and pressure. Several variations of this technique require pretreatment of the sample, heating of the sample in the presence of an alkaline solution and the separation of the solution from the remaining particles [see D. W. Eggimann et al., *Jour. Sediment Petrol.* 50: 215–225 (1980); P. J. Muller et al., *Deep-sea Research*, Vol. 40, No. 3. Pp. 425–444 (1993); D. J. DeMaster, Geophysical Monograph 63: 363–367 (1991); and R. A. Mortlock et al., *Deep-sea Research*, Vol. 36, No. 9, pp. 1415–1426, (1989)].

Methods have been developed for the fractional analysis of marine sediment samples where the elements Ca, Mg, and Sr are associated with the biogenic carbonate fraction and lithogenic fraction [see M. Bender et al., *Micropaleontology*, vol. 21, no. 4, pp.448–459 (1975); and S. R. Taylor, *Geochimica et Cosmochimica Acta*, Vol. 28 pp.1273–1285 (1964)].

The separation of various chemical fractions of phosphorus is of particular interest to biogeochemical researchers [see K. C. Ruttenberg, *Limnol. Oceanogr.*, 37(7), pp. 1460–1482 (1992)]. While fractionation methods have been developed for determining particulate phosphorus found in the water soluble and acid-soluble portion of ocean particles [see G. Liebezeit, *Marine Chemistry*, 33: 61–69 (1991)], the lithogenic P fraction has not yet been precisely characterized by existing methods.

The elements Al, Ti, and Fe that are primarily associated with the lithogenic component of ocean particles have a small but very significant fraction associated with biogenic material and adsorbed/scavenged elements. These fractions have been accessed by several chemical treatments [see K. W. Bruland et al., *Geochimica Cosmochimica Acta*, 58: 3171–3182 (1994); R. W. Murray et al., *Paleoceanography*, Vol. 8, No. 5, pp. 651–670 (1993); and S. B. Moran et al., *Geochimica Cosmochimica Acta*, 55: 2745–2751 (1991)].

The current methods and reaction vessels for extracting elemental constituents from complex solid samples typically involve tedious, multi-stage solution treatments where solid samples must be repeatedly removed, weighed, dried and transferred between successive reaction vessels for extraction and fractionation analysis of individual constituents. Due to repeated sample losses and contamination introduced during multiple sample transfers, such methods generally suffer from a lack of reproducibility, precision and accuracy. Due to the number of treatments and sample transfers typically required, such methods are intrinsically inefficient and due to the considerable sample preparation and transfer times.

It is anticipated that a method which could overcome the limitation of existing fractionation methods and substantially reduce sample transfers, preparation times and costs would be particularly beneficial to the analysis of solid samples in a variety of industrial, environmental and research applications.

SUMMARY OF THE INVENTION

The sequential processing reaction vessel (SPRV) device and method of the present invention provide for accelerated sequential processing of solid samples at high temperatures and pressures within a single reaction vessel. The method employs a series of reagent solution treatments introduced in a microwave transparent, flow-through reaction vessel that retains the solid samples on a membrane filter and frit while permitting introduction and removal of a variety of sample treatment solutions for extraction and fractionation analysis of target analytes.

The SPRV reactor is preferably fabricated with a microwave transparent polytetrafluoroethylene (PTFE) inner vessel and a polyetherimide (sold under the trademark ULTEM®) outer vessel which permit microwave heating of the reactor for accelerated analyte extraction and sample digestion at temperatures up to 150° and pressures up to 150 psi.

The reactor of the present invention provides for rapid sample addition and removal by providing for partial assembly of the reactor housing with retention of a sample membrane filter which facilitates charging of the reactor with solid samples prior to sequential processing solution treatments and eliminates sample transfer losses and contamination during addition of solids to the reactor. A variety of reagent solutions may be sequentially introduced and removed from the innovative reactor of the present invention without disassembly or removal of the solid samples.

During operation of the device of the present invention, pressure can be introduced into the top cover opening to force liquid to pass out the bottom opening. This is an important feature which permits automation of the flow-through system and allows the vessel and sample to remain in the an oven while liquids can be programmed to flow in and out of the vessel. Additional auxiliary openings in the top cover permit the monitoring of reactor temperature and pressure during operation.

The device of the present invention further provides for an innovative laminated membrane filter for retention of solid samples during sequential processing treatment. The use of the innovative laminated filter provides for improved mechanical durability of the membrane when operating at high liquid pressures, eliminates liquid flow by-pass and leakage around the membrane, and maintains high solids retention while permitting pressurized fluid flow through the membrane when discharging reagent liquids at the end of treatment cycles.

The device and method of the present invention provide for efficient accelerated sequential processing of solid samples with a variety of reagent solutions for rapid, low cost fractionation analysis of solid materials with high analytical reproducibility, precision and accuracy and minimum sample losses or contamination due to unnecessary sample transfers.

BRIEF DESCRIPTION OF THE DRAWINGS

This invention is pointed out with particularity in the appended claims. Other features and benefits of the invention can be more clearly understood with reference to the specification and the accompanying drawings in which:

FIG. 2 is a schematic diagram of the laminated membrane filter assembly of the present invention;

FIGS. 4A–4C are schematic diagrams of an SPRV carousel assembly (FIG. 4A), top plate (FIG. 4B) and bottom plate (FIG. 4C);

DESCRIPTION OF THE PREFERRED EMBODIMENTS

1. Introduction

Figures 1A, 1B:
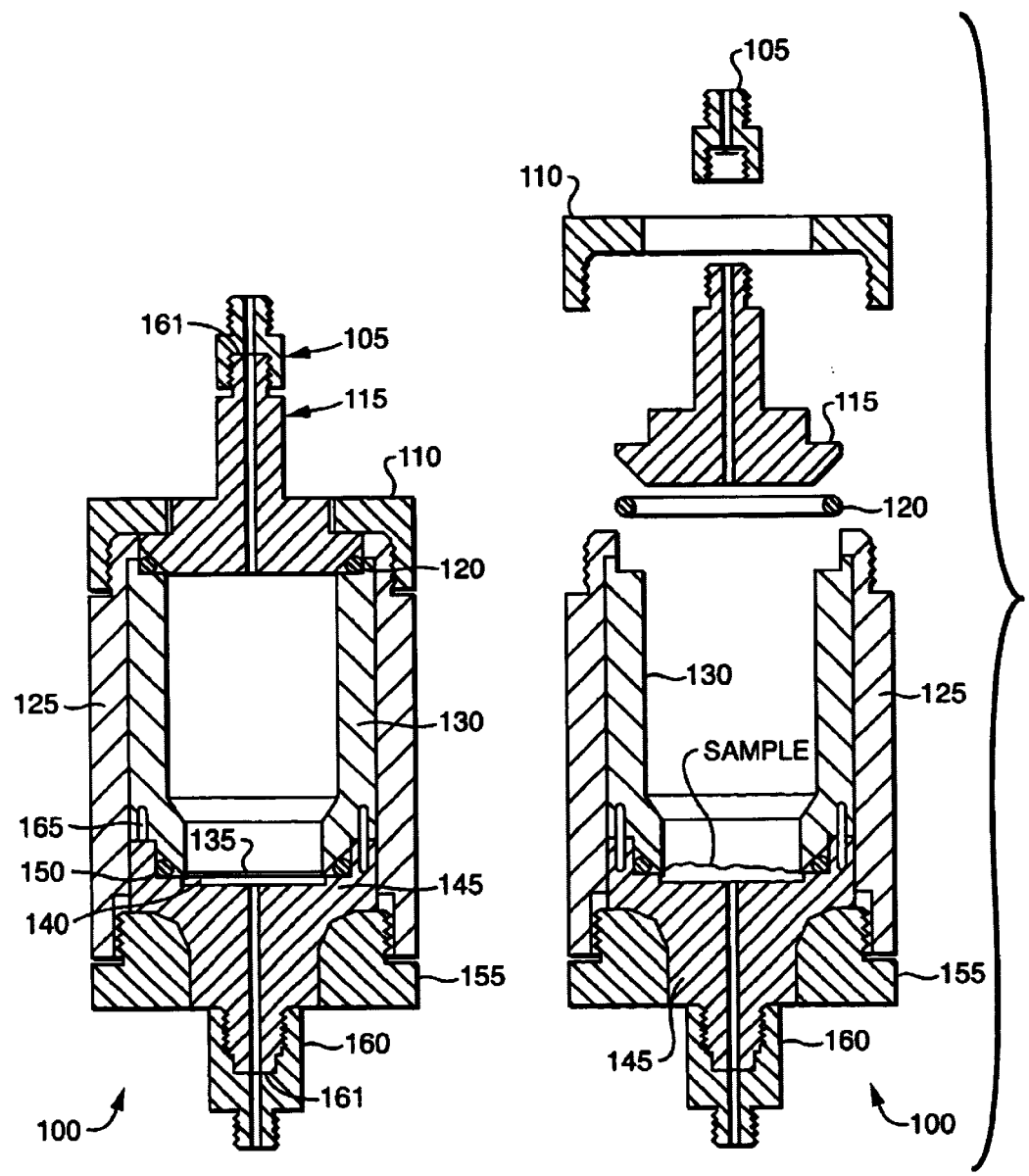
FIGS. 1A–1B are schematic diagrams of cross-sections of the sequential processing reaction vessel of the present invention in a sealed (FIG. 1A) and open (FIG. 1B) position.

In recent years there has been an increasing demand to use sequential extraction methods to quantify elements in a vast number of ocean sediment and particle samples in order to better understand biogeochemical processes, particularly for programs related to global change and paleoproxy research [see R. Chester et al., *Chemical Geology*, 2: 249–262 (1967); C. De La Rocha et al., *Analytical Chemistry*, 68: 3746–3750 (1996); S. Honjo et al., *Deep-Sea Research*, 40: 587–607 (1993); M. Lyle et al., *Geochimica Cosmochimica Acta*, 48: 1705–1715 (1984); R. W. Murray et al., *Paleoceanography*, Vol. 8, No. 5, pp. 651–670 (1993); and D. M. Nelson et al., *Global Biogeochemical Cycle*, 9, 359–372 (1995)]. One of the important examples of applications of a sequential extraction method is to distinguish concentrations of biogenic silicates (diatom frustules) from lithogenic silicates (clay minerals and structural silicates) in ocean sediment material.

When applying conventional extraction methods, sample throughput is constrained due to the considerably slow reaction times and numerous time consuming sample transfers required with successive chemical treatments [see R. J. Collier et al., *Marine particles: Analysis and Characterization*, (ed.) D. C. Hurd et al., AGU Geophysical Monograph 63 (1991); D. W. Eggimann et al., *Jour. Sediment Petrol.* 50: 215–225 (1980)]. In order to overcome these limitations, an innovative sequential processing reaction vessel (SPRV) has been developed that eliminates the typical sample transfer processes, losses and contamination encountered with conventional reactor devices and methods and substantially reduces sample processing time by facilitating rapid, sequential solution treatments and analyte fractionation and extraction from solid samples.

With the SPRV device and method of the present invention, a sample remains in a single reaction chamber throughout sequential reaction with a variety of chemical reagents. The SPRV device and method of the present inventions dramatically reduces the handling operations and processing time associated with conventional sequential extraction methods which employ multiple sample transfers, centrifugations and filtrations. With the present SPRV device and method, sources of sample contamination and material losses, for example sample transfers, incomplete solids separation by centrifugation and sample removal from filters are eliminated. The device and method provide for rapid sequential treatment of solid samples with a variety of reagents over a range of reaction temperatures and pressures which accelerate reaction and extraction of sample analytes. Solutions instantly reach the desired temperatures when they are heated in a microwave oven which accelerates reaction times. The heating rate, temperature, pressure, and time for sample treatments may be programmed with comercially available microwave ovens. Thus, the innovative device and method of the present invention significantly reduces the time required to extract analytes and sequentially treat samples with a series of reagent solutions when compared to existing methods. For example, results from SPRV experiments show that the time required to dissolve biogenic Si from sediment sample PB 123 in heated 1M $Na_2CO_3$ solution with the present device and method was reduced from 4 hours to 30 minutes.

2. SPRV Design

A schematic of the SPRV 100 is provided in FIGS. 1A and 1B. As shown in FIG. 1A, the SPRV 100 comprises a top valve 105, a top securing collar 110, a top cover 115, a top cover O-ring 120, an exterior jacket 125, an interior liner 130, a membrane filter 135, a filter support frit 140, a filter holder 145, a filter holder o-ring 150, a bottom securing ring 155, a bottom valve 160 and alignment pins 165. While FIGS. 1A and 1B show only a single top valve 105, the top cover 115 may be equipped with additional auxiliary ports 116a, 116b for temperature or pressure probes used for measuring reaction chamber conditions. The interior volume formed by the top cover 115, interior liner 130 and filter holder 145 of the SPRV is referred to herein as the reaction chamber. In one embodimnent, the exterior dimensions of the SPRV 100 are 16 cm high with a 6.5 cm diameter and a reaction chamber volume of 50 ml.

The SPRV 100 interior parts that come in direct contact with the sample and solutions are preferably made of a perfluoroalkoxy-polytetrafluoroethylene copolymer material, sold under the trademark TEFLON® PFA, and all SPRV 100 exterior parts required for strength are preferably made of a polyetherimide material, sold under the trademark ULTEM®. FIGS. 1A and 1B show one SPRV 100 embodiment where the interior parts, comprising a top valve 105, a top cover 115, an interior liner 130, a filter holder 145 and bottom valve 160, are made of a polytetrafluoroethylene material, sold under the trademark TEFLON®, and the exterior parts, comprising a top securing collar 110, an exterior jacket 125 and a bottom securing ring 155, are made of a glass-filled polyetherimide material, sold under the trademark ULTEM® 2300. Other materials may be employed as long as they are chemically resistant to treatment solutions and transparent to microwave energy so that they may be used in a microwave oven. One innovative design feature of the SPRV 100 is the incorporation of the filter holder 145 within the housing of the SPRV 100. With this design, tightening of the bottom securing ring 155 threads on the exterior jacket 125 urges the filter holder 145 against interior liner 130 thereby compressing the filter holder O-ring 150 against the membrane filter 135, interior liner 130 and filter holder 145 and providing a leak-proof seal that withstands both the high temperatures and high pressures generated during operation of the SPRV 100.

While any suitable membrane filter 135 and filter frit support 140 materials may be employed, in preferred embodiments hydrophylic PTFE or hydrophylic polytetrafluoro-ethylene, sold under the trademark TEFLON®, filters 135 and frit supports 140 are employed due to their wetting characteristics, chemical inertness and mechanical stability at high temperature and pressure. In alternative embodiments, hydrophobic PTFE may be employed as filters 135 and frit supports 140 providing the material is either pretreated with a wetting promoter solution or coated with a hydrophylic material. Testing of PTFE filter materials showed that they retained their integrity at reaction temperatures up to 150° C., reaction pressures up to 150 psi and at liquid flow pressures up to 30 psi. Other filter materials may be employed as long as they similarly possess these desirable properties. Where lower reaction temperatures are employed, alternative filter 135 and frit support 140 materials may be utilized. For example cellulosics, polyamides, acrylics, polyesters, styrenics, fluoropolymers, polyolefins or inorganics may be employed as alternative filter membrane 135 materials for lower temperature treatments. Similarly, high density polyethylene, ultra high molecular weight polyethylene, polypropylene, polyvinylidene fluoride, polystyrenes, ethylene vinyl acetate and polysulfone may be employed as alternative filter frit support 140 materials with lower temperature treatments.

While membrane filter 135 pore size may be selected based on either sample particulate size or digestion behavior, in preferred embodiments, membrane filters 135 having a pore size ranging from 0.45 to 3 microns are employed with particulate samples. In a preferred embodiment, a hydrophilic, PTFE, 0.5 um pore size, Millipore LCR Membrane Filter (Millipore Corp., Bedford, Mass.) is employed as the membrane filter 135 with perforated or porous 1/16 to 1/8 inch thick PTFE disk as a filter support frit 140. In the most preferred embodiment, an innovative laminated membrane filter 135 is employed which provides for improved filtration by eliminating fluid bypass and leakage around membrane filter edges, high solids retention by the 0.5 um LCR membrane filter, high fluid throughput through the 37 um PTFE filter, and enhanced mechanical strength for the fragile LCR membrane filter at fluid flow pressures up to 30 psi.

In this preferred laminated filter embodiment, a 0.5 um LCR Membrane Filter is first cut into a toroidal shape with a nominal 37 mm diameter and nominal ring width of 3 to 5 mm. This ring-shaped piece is then placed over a second 37 mm diameter, 0.5 um LCR Membrane Filter which is then placed over a 37 mm diameter, 37 um pore size PTFE filter. The outside perimeter of the three layers are then fused together by pressing the layers between two metal plates at 330° C. for 15 minutes. This treatment produces a fused, bonded non-porous PTFE outer ring around the outside perimeter of an unbonded central area of the LCR and 37 um filter and retains the 0.5 um pore size of LCR filter and the 37 um pore size of the PTFE filter. A schematic diagram of the laminated filter assembly is provided in FIG. 2. The resultant laminated membrane filter 135 is placed in the SPRV 100 with the LCR filter facing the top and the 37 um PTFE filter facing the bottom of the vessel 100.

The innovative laminated membrane filter of the present invention offers distinct advantages over conventional supported membrane filters which typically fuse a low pore size membrane filter to a coarser pore size support over the entire surface of the membrane. In these conventional supported membrane filters, the filtration pore size and performance of the membrane filter is typically compromised by the fusion treatment which typically bonds the entire surface of the membrane filter to its support and generally results in undesirable pore blockage across the entire membrane filter-support interface leading to lower fluid permeability and higher pressure buildup across the membrane filter which leads to premature membrane rupture. With the innovative laminated membrane filter of the present invention, only limited area on the outside perimeter of the membrane is fused, leaving most of the membrane filter surface and membrane support surface in their pristine state, thereby preventing pore blockage. Additionally, after fusion of the laminate, the fused ring on the outside perimeter forms a non-porous, compressible layer that extends beyond the filter holder o-ring 150 and compresses with the O-ring 150 during assembly of the SPRV 100 to form a tight, leak-proof seal which prevents undesirable liquid flow bypass and leakage around membrane filter perimeter at high reactor or fluid pressures.

A cross section of the SPRV 100 configuration during sample loading is shown in FIG. 1B. By providing an independent means for securing the membrane filter 135 with the bottom housing members 130, 145 and o-ring 150, the innovative SPRV 100 design enables removal of the top securing collar 110 and top cover 115 for immediate access to the SPRV 100 reaction chamber for introduction of solid samples onto the membrane filter 135 through a large chamber opening at the top of the vessel. During operation the SPRV 100 is sealed (see FIG. 1A) and liquids can be introduced into the reaction chamber by opening the top valve 105 and removed from the chamber by opening the bottom valve 160. The top and bottom valves 105, 160 thus provide for either continuous flow of liquid reactants through the chamber or the sequential addition of fluid reactants and extraction of analyte solutions during batch sample treatments without opening the vessel or removing and replacing samples. The valve cap openings 105, 160 at the top and bottom of the SPRV 100 enable either pressure or vacuum to be applied to the reaction chamber to separate the liquid from sample solids retained on the filter 135. As shown if FIGS. 1A and 1B, both the top 105 and bottom 160 valves incorporate a safety pressure relief seal 161 which ruptures in the event of excessive internal pressure during heating.

While the SPRV 100 may be heated with conventional convection or radiant heat sources, in a preferred embodiment, the reaction vessel 100 is configured for heating in a microwave oven equipped with reaction chamber sensors for continuous monitoring of vessel 100 temperatures and pressures. In a preferred embodiment, the vessel 100 is heated in a CEM MDS-2100 programmable microwave oven (CEM Corp., North Carolina). The MDS-2100 is equipped with an inboard pressure control system to monitor and control pressure conditions inside the SPRV 100 reaction chamber. A pressure sensing line is fed through either the top valve 105 port or an auxiliary port 116a on the top cover 115. Pressure is measured by a pressure transducer and displayed graphically and digitally on an LCD display. The MDS-2100 oven is also equipped with a fiber optic probe used to monitor and control SPRV reaction chamber temperature. A microwave transparent fiber optic temperature probe is fed through either a top valve 105 port or an auxiliary port 116b on the top cover 115. The temperature sensor is a phosphor which emits fluorescent light after excitation by an optical source. The decay rate of fluorescent emission is temperature dependent and provides for accurate and precise determination of the vessel 100 temperature. Details of the pressure and temperature sensor are provided in the MDS-2100 Operation Manual (CEM Corp., Matthews, N.C., 1994).

3. SPRV Operation

In a typical operation of the SPRV 100, an approximately 10 mg sample is introduced into the partially assembled reaction chamber (see FIG. 1B) through the top opening of the vessel. The top cover 115 and top valve 105 are then secured to the external and interior housing members 125, 130 with the top securing collar 110 (see FIG. 1A). With the bottom valve 160 closed, approximately 10 ml to 40 ml of treatment solution is introduced into the reaction chamber by opening the top valve 105. The treatment solution can include any organic and inorganic reagents, acids, bases or solvents. The top valve 105 is closed and the sealed SPRV may then be heated by an external heat source up to 150° C. Due to the heating of the liquids to elevated temperatures in the enclosed reactor, pressures as high as 150 psi may be achieved. This combination of high reaction temperatures and pressures provide for accelerated reaction of the sample with treatment solutions. In one preferred embodiment, the vessel is heated at a rate of 1° to 2° C. per minute to approximately 120° C. at 40 to 50 psi and held at temperature for about 15 minutes. Other heating rates, reaction temperatures and pressures may be readily employed by the skilled artisan based on the specific reagents used and sample reaction requirements. While conventional radiant heating or convection ovens may be employed for heating the SPRV 100, in a preferred embodiment the vessel and sample are microwave-heated in a programmable microwave oven. With this embodiment, rapid heating and cooling of the enclosed sample and reagents is achieved due to the microwave transparency of the SPRV 100 and microwave absorption by the sample and reactants.

After reaction of the treatment solution with the sample at high temperature and pressure, the treatment solution containing extracted analytes is separated from the residual sample solids by the filter 135 and removed from the reaction chamber by draining the solution through the bottom valve 160. In a preferred embodiment, the fluid is pressurized by introducing compressed nitrogen gas through the top valve 105 so as to force the liquid through the filter 135 and out of the chamber through the bottom valve 160. The filter 135 retains any remaining sample solids within the chamber for subsequent treatments. In a preferred embodiment, a laminated 0.5u PTFE membrane filter is employed due to its inertness, strength, and ability to retain remaining fine particles. The chamber may be subsequently rinsed with the treatment solution, distilled water or solvent to flush any remaining reactants and extracted analytes from the reaction chamber.

Figure 3:
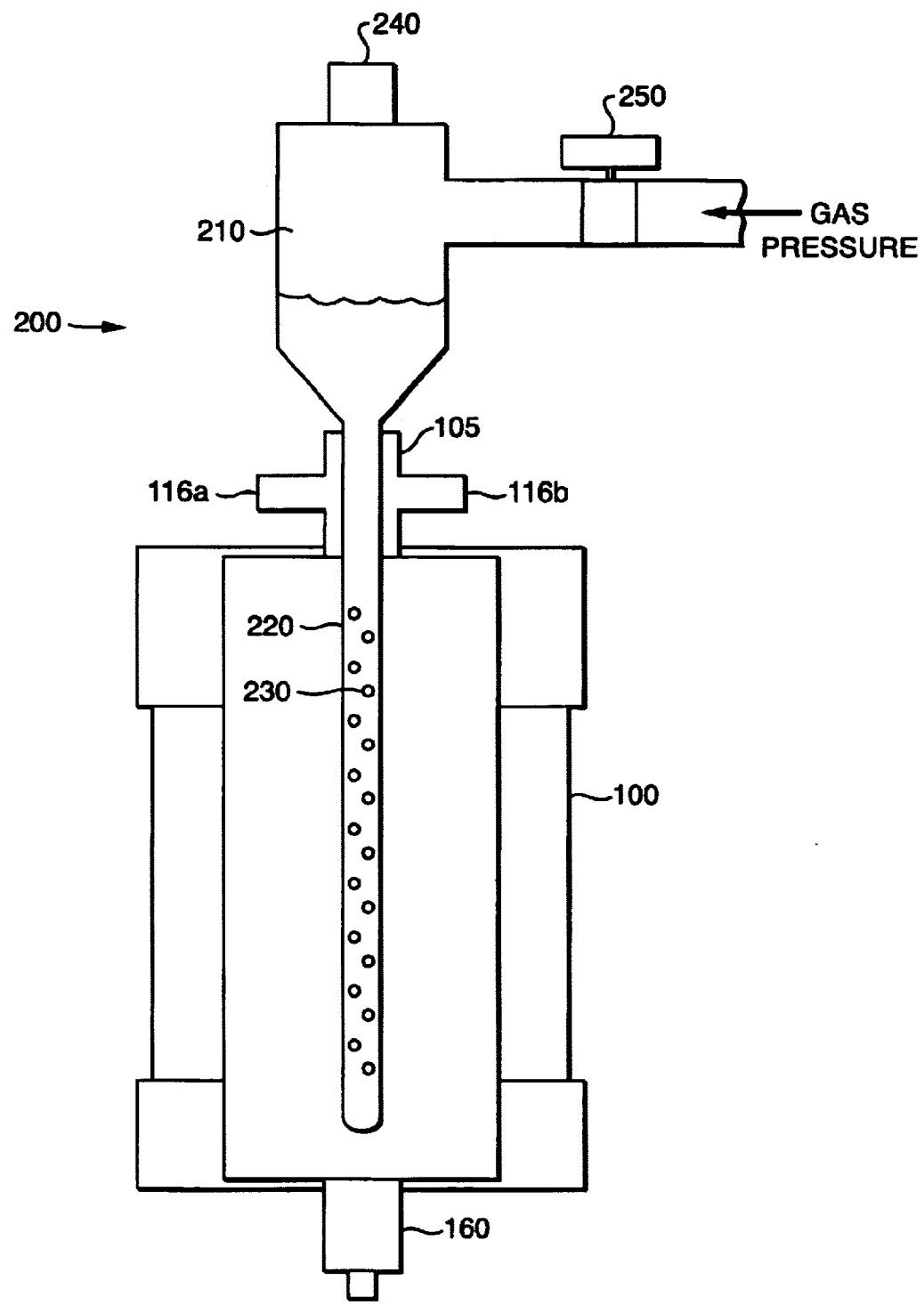
FIG. 3 is a schematic diagram of the liquid spray attachment for the SPRV of the present invention.

FIG. 3 shows a schematic diagram of a liquid spray attachment 200 which is typically employed either to add liquid reagents to the reaction chamber prior to a treatment cycle or to rinse the chamber at the end of a solution treatment. The spray attachment 200 comprises a spray tube 220 with one closed which is inserted into the vessel 100 through the top valve port 105. The inserted tube 220 has a plurality of holes 230 machined along its length and perimeter. The tube 220 is connected to a liquid reservoir 210 which is filled with liquids through an entry cap 240. The cap 240 is equipped with a septum for injecting liquids with a syringe. A gas valve 250 is attached to the side of the reservoir 210 for introducing gas pressure to urge liquid in the reservoir 210 through the tube 220 and spray holes 230. The resultant liquid spray is uniformly distributed within the reaction chamber of the vessel 100 during filing and rinsing of the SPRV 100 before and after solution treatments. After rinsing of the vessel 100, additional solution or solvent may be added to the extracted liquid for adjusting analyte concentrations to a known volume. Typical analyte volumes range between 10 ml to 50 ml for treatments of 10 mg samples and the volume is adjusted to establish analyte concentration for optimum analysis using preferred analytical methods. The extracted solution and analytes may be directly analyzed by conventional spectrographic analytical methods. The entire process may be repeated for reacting additional alternative reagent solutions with the remaining sample solids according to desired sequential processing procedures which are selected for the sample and analytes of interest.

FIGS. 1A and 1B show an example of an SPRV filter holder assembly. Typically, the bottom portion of the SPRV vessel 100, comprising the jacket 125, securing ring 155 and filter holder assembly, is initially assembled (see FIG. 1B). As shown in FIGS. 1A and 1B, the membrane filter 135 is held in position by the o-ring 150, interior liner 130, filter holder 145 and alignment pins 165. If hydrophobic filters 135 are employed, they are wetted and rinsed with acetone or alcohol. Where vacuum is used, there is no need to secure the top valve cap 105. A vacuum of 200 mm of Hg is introduced in the SPRV vessel 100 by loosening the bottom valve cap 160. As vacuum is applied, liquid is drawn through the vessel 100 and filter 135 and the filtrate is collected in the evacuated vessel 100. Where pressure is used, a top valve cap 105 must be attached. Both the top 105 and bottom 160 valves must be open to filter the vessel contents. Typically, 30 psi air pressure is introduced through the top valve cap 105 and liquid is forced through the vessel 100 and filter 135 and collected in a container under the bottom valve cap 160.

Prior to sealing the SPRV vessel 100, the filter 135 is rinsed with distilled water to remove wetting solution and to reduce static problems when introducing samples to the vessel 100. Approximately 10 mg of sample is weighed and placed at the bottom of the vessel on top of the filter 135 (see FIG. 1B). After securing the top valve cap 105, the SPRV vessel 100 is ready for introduction of the solution treatments. After removal of the top vent fitting 161, solutions are added to the vessel 100 through the opening in the top valve cap 105. The vent fitting 161 is secured and the procedures for the first solution treatment is followed. If heating is required, a single opening valve cap 105 is used for conventional heating and a triple opening valve cap is used for microwave heating. The additional openings used with microwave heating are for monitoring vessel 100 temperature and pressure. Following the heating treatment, the vessel 100 is cooled to room temperature prior to filtration. The filtrate is then withdrawn by either application of vacuum or pressure as noted above. For sequential treatments, additional solutions are introduced at the top valve 105 and the process is repeated for each treatment solution. An example treatment solution sequence is provided in Table 1.

After the entire treatment process is completed, the last treatment solution is separated from the remaining particles by introducing gas pressure from a pressurized source into the reaction chamber at the top valve 105 and draining the solution through the filter 135 and collecting it from the bottom valve 160.

4. Multiple SPRV System

Sample throughput can be optimized by applying a multiple SPRV system to a large number of samples with the expectation of uniform results. The design and construction of a Multiple SPRV System enables processing a large number of samples simultaneously and results in a substantial reduction in processing time and costs compared to existing sample preparation methods. The Multiple SPRV System consists of a plurality of SPRV units (FIG. 1A) arranged on carousel assemblies 300 (see FIGS. 4A–4C). In one embodiment, a Multiple SPRV System for processing 20 samples simultaneously may be employed. In alternative embodiments, the number of SPRV units 100 and carousels 300 may be varied to meet heating oven requirements. By increasing sample throughput, a Multiple SPRV System provides for significantly improvements in time and cost of elemental analysis of sediment, slurry or particulate samples while improving accuracy, precision, and reliability of analytical results when compared to existing procedures.

Figure 4B:
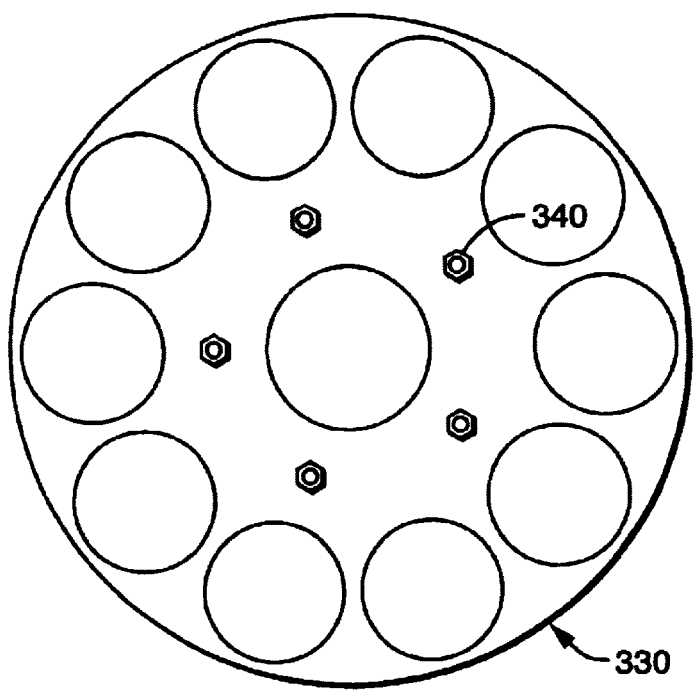
Figure 4C:
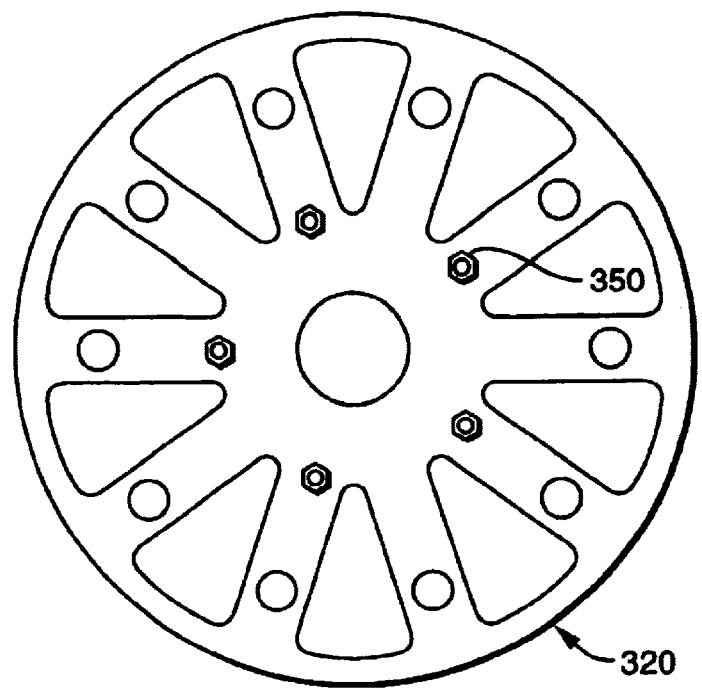
Figure 5A:
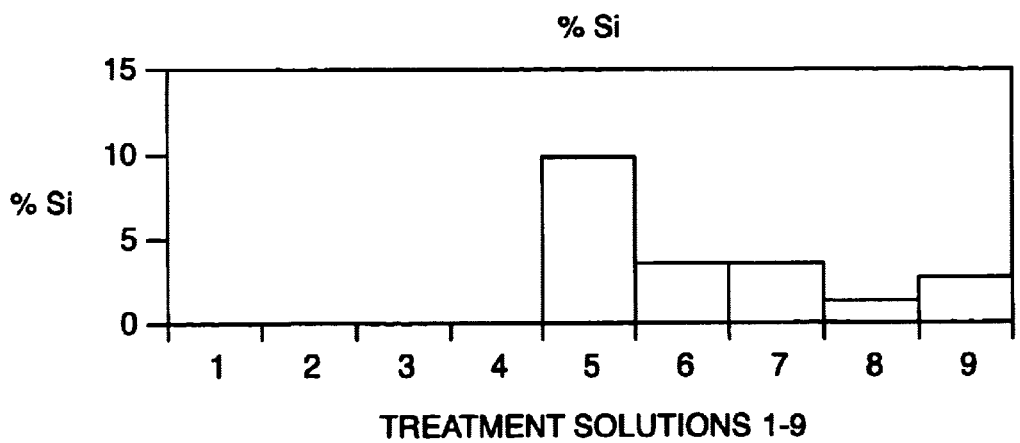
FIGS. 5A–5E show sequentially extracted elemental concentrations in treatment solution 1 through 9 for a Panama Basin sediment trap sample.
Figure 5B:
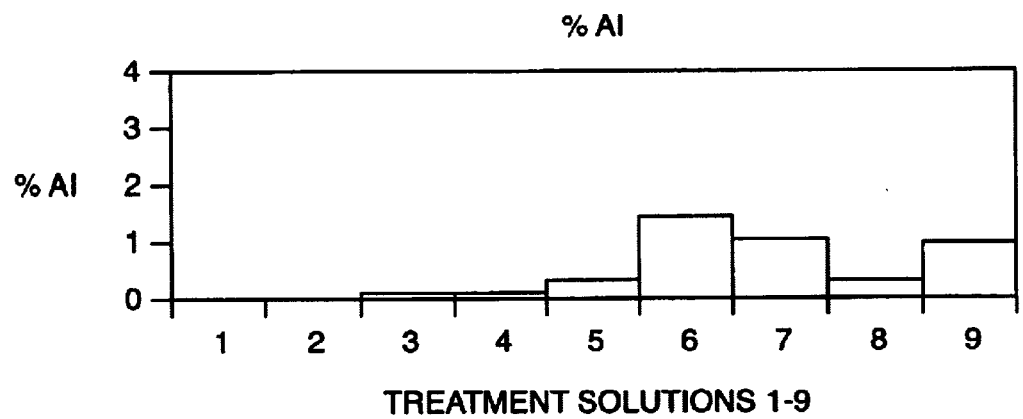
Figure 5C:
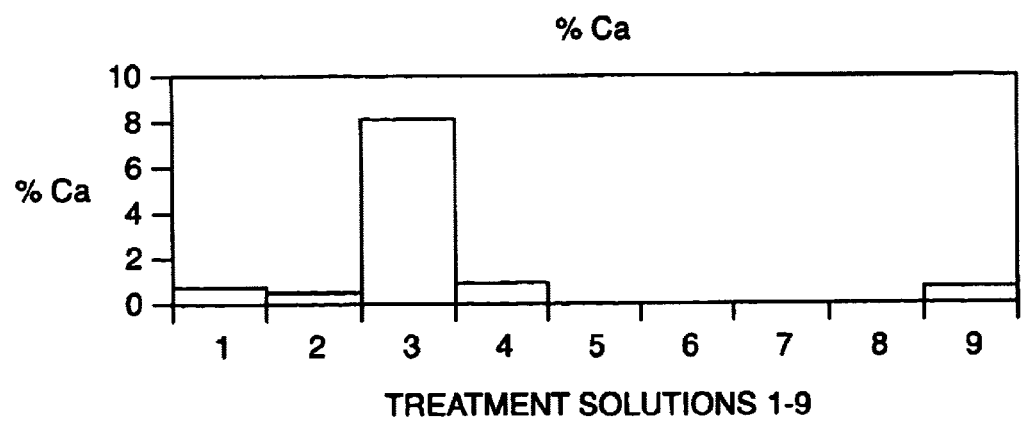
Figure 5D:
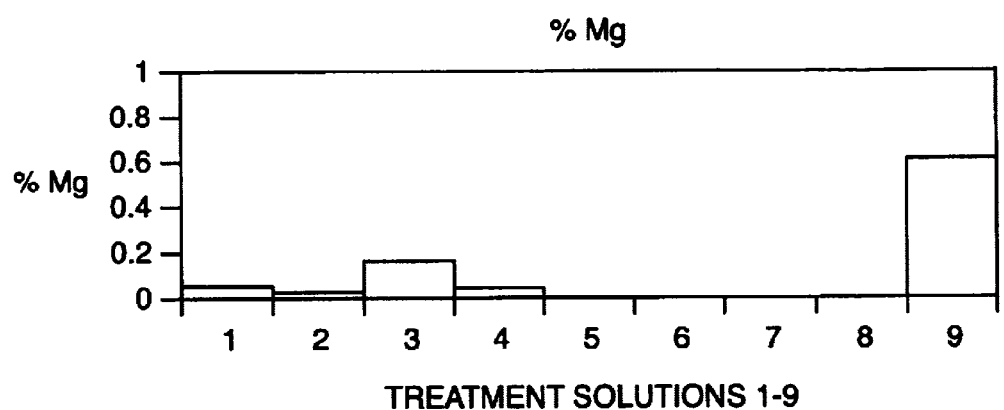
Figure 5E:
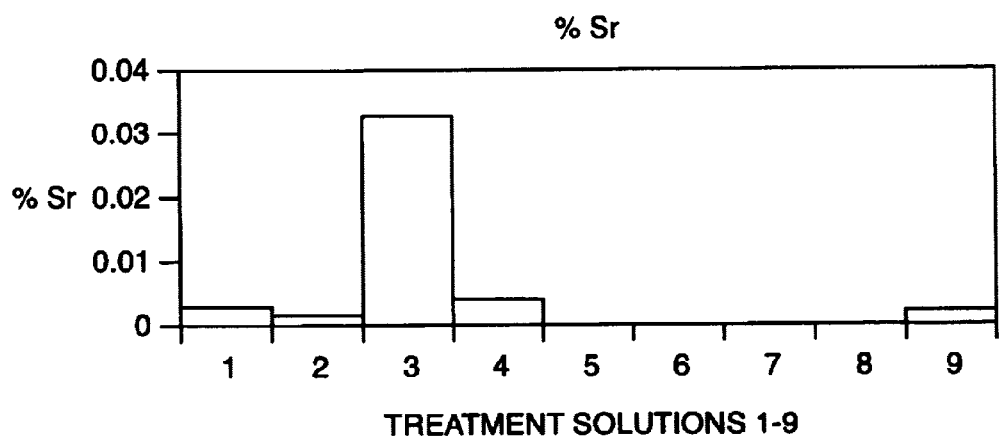
Figure 6A:
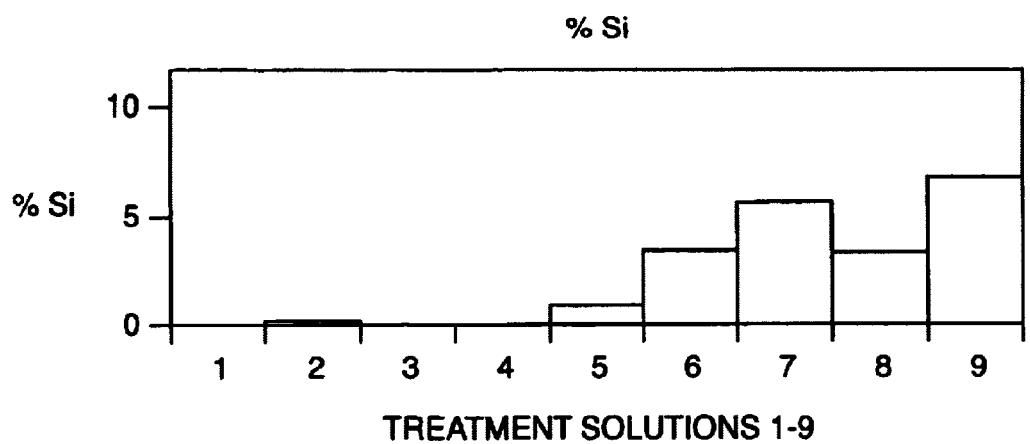
FIGS. 6A–6E show sequentially extracted elemental concentrations in treatment solution 1 through 9 for a Southern Ocean deep ocean surface sediment sample.
Figure 6B:
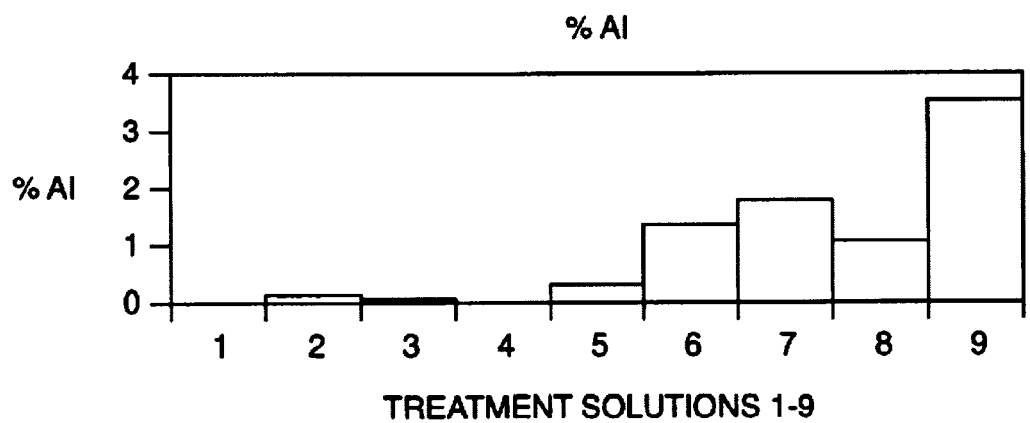
Figure 6C:
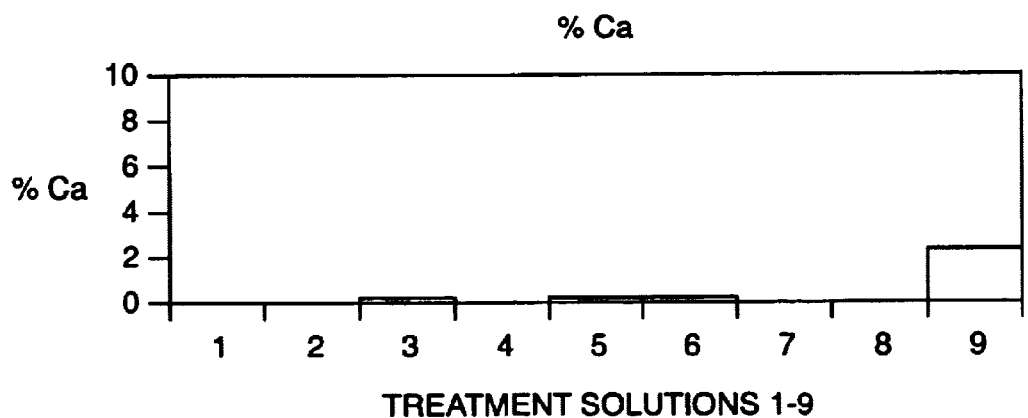
Figure 6D:
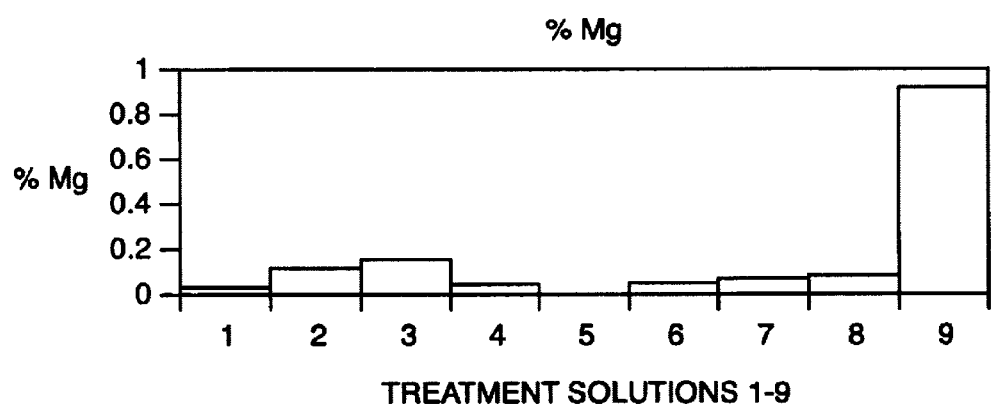
Figure 6E:
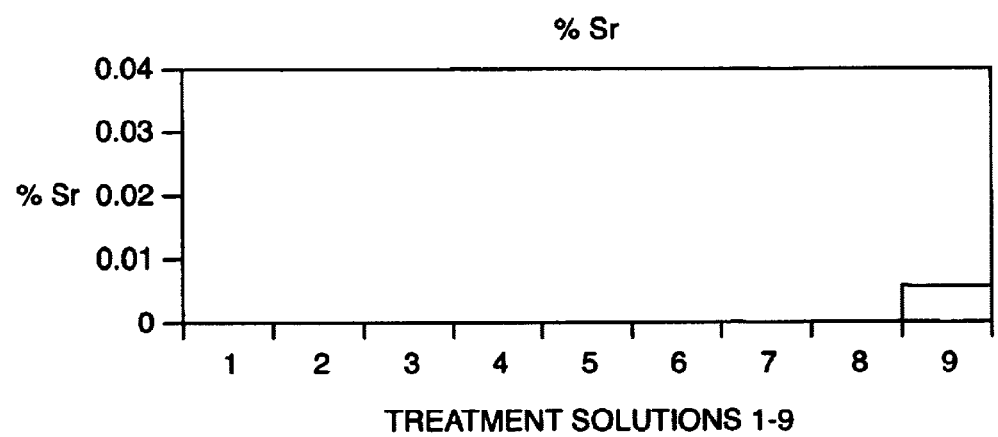

As shown in FIGS. 4B–4C, the carousel 300 is typically machined from UHMW polyethylene to accommodate a plurality of SPRV reactors 100. In one embodiment, the carousel comprises a support pedestal 310, which is configured to mount on a rotating pedestal mount 305 of a microwave oven 301. A carousel bottom plate 320 is attached to the support pedestal 310 with a series of bolts 345 (not shown) passing through the botom plate bolt holes 350 The carousel top plate 330 is similarly attached to the support pedastal 310 with a series of bolts 345 (not shown) passing through the top plate 330 bolt holes 340. The carousel bottom plate 320 is machined with a plurality openings configured to register with the SPRV bottom valve assembly 160. The carousel top plate 330 is machined with a plurality of openings configured to register with the SPRV exterior jacket assembly 125. In one embodiment, each SPRV carousel assembly 300 holds ten SPRVs 100 and is designed to attach to the rotating pedestal of a programable microwave oven (see FIG. 4A). In alternative embodiments, both the number of SPRVs per carousel and the number of carousels employed can be varied and their respective dimensions may be adapted to conform to the interior dimension of the microwave oven. During microwave heating the SPRV carousel is alternately rotated clock-wise and counterclockwise 360 degrees so that microwave heating is uniform for all the SPRV vessels. The carousels and SPRVs are easily removed and interchange so that while one multiple SPRV-carousel assembly is being processed, unmounted SPRV-carousel assemblies can be prepared offline for the next treatment cycle.

To evaluate the Multiple SPRV System, a variety of solution treatment methods and conditions, as noted in the section below, may be applied to selected reference samples. For example, a combination of four separate solution treatments may be employed which include acidic and alkaline solution treatments as well as elevated temperature and pressure treatments on sediment reference materials of well known composition. The Multiple SPRV System permits simultaneous testing of various sediment reference materials during complex sequential chemical treatments. The multiple station device provides for replicate samples and reagent blanks to be simultaneous processed with a series of complex sequential treatments to determine the analytical precision of elemental analysis during multi-sample processing. Known total elemental analysis on sample reference materials enables mass balances to be calculated for each sample to monitor the complete recovery of partitioned elements.

5. Sequential Extraction Methods

Sequential extraction methods have been developed to address specific questions for enhanced understanding of elemental behavior in complex oceanographic and geological samples [see R. Chester et al., *Chemical Geology*, 2: 249–262 (1967); A. Tessler et al, *Analytical Chemistry*, 51(7): 844–850 (1979); D. W. Eggimann et al., *Jour. Sediment Petrol*. 50: 215–225 (1980); J. M. Robbins et al., "A Sequential Extraction Procedure for partitioning elements amoung co-existing phases in marine sediments", College of Oceanography, Oregon State University, Ref.#84–3, 64pp. (1984); S. B. Moran et al., *Geochimica Cosmochimica Acta*, 55: 2745–2751 (1991); and R. Chester et al., *Journal of the Geological Society, London*, 151: 351–360 (1994)]. While numerous reaction methods and treatments may be combined in varying sequences to develop sequential processing methods for specific sample types and target analytes in a variety of geological, marine, environmental, research and industrial applications, four example sequential processing and fractionation methods are provided below as typical example applications for which the SPRV device and method of the present invention are particularly suitable.

Method 1: Techniques most commonly used for the chemical fractionation of Si in biogenic and lithogenic sedimentary particles are based on the higher solubility of biogenic silica in alkaline solutions at elevated temperature and pressure. Several variations of this technique require pretreatment of the sample, heating of the sample in the presence of an alkaline solution and the separation of the solution from the remaining particles [see D. W. Eggimann et al., *Jour. Sediment Petrol*. 50: 215–225 (1980); P. J. Muller et al., *Deep-sea Research*, Vol. 40, No. 3. Pp. 425–444 (1993); D. J. DeMaster, Geophysical Monograph 63: 363–367 (1991); and R. A. Mortlock et al., *Deep-sea Research*, Vol. 36, No. 9, pp. 1415–1426, (1989)]. It is anticipated that the SPRV device and method of the present invention will radically simplify the complex and lengthy procedures of the existing methods and substantially reduce reaction time for dissolving the biogenic Si in alkaline solutions. Method 2: In marine sediment samples the elements Ca, Mg, and Sr are associated with the biogenic carbonate fraction and lithogenic fraction [see M. Bender et al., *Micropaleontology*, vol. 21, no. 4, pp.448–459 (1975); and S. R. Taylor, *Geochimica et Cosmochimica Acta*, Vol. 28 pp.1273–1285 (1964)]. Since these elements are also major constituents of seawater, significant analytical corrections are required if removal of seawater from the solids is incomplete [see R. J. Collier et al., *Marine particles: Analysis and Characterization*, (ed.) D. C. Hurd et al., AGU Geophysical Monograph 63 (1991)]. It is anticipated that the SPRV device and method of the present invention will allow effective pretreatment of the sediment to remove seawater prior to analysis, thereby eliminating the need for sea-salt corrections [see M. Lyle et al., *Geochimica Cosmochimica Acta*, 48: 1705–1715 (1984)]. It is anticipated that innovative treatments removing the carbonates from the lithogenic fraction in these samples may be possible with the SPRV device and method.

Method 3: The separation of various chemical fractions of phosphorus is of particular interest to biogeochemical researchers [see K. C. Ruttenberg, *Limnol. Oceanogr.*, 37(7), pp. 1460–1482 (1992)]. Particulate phosphorus is found in the water soluble and acid-soluble portion of ocean particles [see G. Liebezeit, *Marine Chemistry*, 33: 61–69 (1991)] while the lithogenic P fraction has not yet been precisely characterized by existing methods. It is anticipated that the SPRV device and method of the present invention will facilitate chemical fractionation of these multiple forms of phosphorus due to the improved chemical partitioning methods offered.

Method 4: The elements Al, Ti, and Fe that are primarily associated with the lithogenic component of ocean particles have a small but very significant fraction associated with biogenic material and adsorbed/scavenged elements. These fractions have been accessed by several chemical treatments [see K. W. Bruland et al., *Geochimica Cosmochimica Acta*, 58: 3171–3182 (1994); R. W. Murray et al., *Paleoceanography*, Vol. 8, No. 5, pp. 651–670 (1993); and S. B. Moran et al., *Geochimica Cosmochimica Acta*, 55: 2745–2751 (1991)]. It is anticipated that precise sequential chemical treatments and fractionation can be achieved with the SPRV device and method of the present invention. Additionally, the complete dissolution of the most resistant solid phases may be achieved by adapting Totland's method [see Totland et al., *Chemical Geology*, 95: 35–62 (1992)] and employing strong acids and microwave heating with the SPRV device of the present invention.

While the SPRV device and method may be applied to any one of the tedious analytical determinations described above in realizing significant cost and time savings over the existing methods, the SPRV device and method uniquely provides for combining all four analytical methods for sequential processing of samples within a single reaction vessel to provide elemental fractionation, extraction and analysis of complex sample chemical constituents with both a substantial savings in processing time and expense as well as a corresponding improvement in analytical accuracy and reproducibility due to elimination of transfer losses and contamination.

EXAMPLE 1

Two ocean sediment reference materials of different component composition were treated in the SPRV with four treatment solutions at elevated temperatures and pressures. The two ocean sediment reference materials were marine particulate samples collected by a sediment trap in the Panama Basin (PB123) consisting primarily of biogenic components (i.e. carbonate, biogenic silicate and organic components) and a deep ocean surface sediment sample from the Southern Ocean (PC40) consisting primarily of lithogenic particles (i.e. clay minerals and structural silicates). Replicates of four samples were processed for each sample type. For these samples, a total of nine sequential treatments were employed, including: a) two distilled $H_2O$ treatments at room temperature; b) two treatments of 1N acetic acid at room temperature; c) four treatments of 1M $Na_2CO_3$ at elevated temperatures 90° C., 120° C., 150 C., and 150° C.; and one treatment of $HNO_3$/HF at 150° C. Details of the sequential treatments are provided in Table 1.

The treatment solutions of Table 1 were chosen because they extract elements associated with the major components of ocean sediment material. The elements associated with water soluble and sea water component are expected to be predominantly in treatment solutions 1 and 2. The elements associated with the carbonate component are expected to be predominantly in treatment solutions 3 and 4 treated with 1M acetic acid. The elements associated with the biogenic silicate component with minor contributions from the lithogenic component are expected to be predominantly in treatment solutions 5–8. The elements of the remaining lithogenic component are expected to be completely dissolved by the $HNO_3$/HF treatment and contained in treatment solution 9. Major and minor elements for each sample solution, including Ca, Mg, Sr, Si, and Al, were analyzed by ICP-ES. The analytical results for each treatment solution utilized with the two samples are provided in FIG. 5.

Results from the elemental concentrations in the nine treatment solutions and microscopic examination of the filters indicate that all particulate material was removed from the filter by the nine sequential treatments. As shown in FIG. 5, the elements associated with the major components of ocean sediments were extracted into the expected treatment solutions. For example, with the PB 123 sample, high concentrations of Si were detected in 1M $NA_2CO_3$ solutions 5–7 indicating the biogenic silicate component. Furthermore, with this sample high concentrations of Ca, Mg and Sr, representing the carbonate component, were detected in the in acetic acid solutions 3 and 4. In contrast, with the PC40 sample, the majority of elements were detected in solution 9, indicating dissolution of the resistant lithogenic component by the $HNO_3$/HF treatment. While sequential extraction techniques may have limitations regarding interpretation of element extraction behavior due to sample composition and element chemical properties [see J. M. Martin et al., *Marine Chemistry*, 22: 313–341 (1987); and C. Kheboian et al., *Analytical Chemistry*, 59: 1417–1423 (1987)], as the results shown in FIG. 5 demonstrate, the unique advantages and efficiencies of the SPRV reactor and its associated processing methods have clearly demonstrated its use as an invaluable tool for fractionating elements in solid samples and providing total analysis of solid samples with high reproducibility and accuracy.

EXAMPLE 2

A series of SPRV tests were performed to compare conventional convective heating with microwave heating when dissolving biogenic Si in heated alkaline treatment solutions. The chemical fractionation of biogenic and lithogenic sedimentary particles was conducted based on the higher solubility of biogenic silica in alkaline solutions at elevated temperature and pressure. Three reference samples containing biogenic Si as the primary component were utilized to evaluate the efficiency of alternative alkaline solution treatments: a) sediment trap diatoms with some radiolarians (AE-2-3); b) core sample radiolarians with traces of diatoms (JB rads); and c) core sample diatoms with some radiolarians (P26).

Approximately 5 to 10 mg of sample was placed in the SPRV reaction chamber with 10 ml of 1 M $NA_2CO_3$ and heated (a) with a conventional convection oven, with shaking every 30 min, at constant temperatures of 90° C., 120° C. and 150° C. for four hours, and (b) with a microwave oven programmed for 10 minute heating at 90° C., 120° C. and 150° C. After treatment, samples were examined under a light microscope to determine the presence or absence of biogenic particles. The test results indicate that biogenic Si in sediment trap reference material (AE-2-3) dissolved after four hours treatment in a conventional oven at 90° C. as anticipated while microwave heating dissolved the sample in 10 minutes at 120° C. The biogenic Si in reference core materials (Jb rads and PC26) were never completely dissolved with four hours heating at 120° in the conventional oven but were completely dissolved in 10 minutes heating at 120° C. with microwave heating.

TABLE 1

Treatment Solution Sequence

| TREATMENT SOLUTIONS | Vol. (ml) | Temp. (° C.) | Time (min.) | ELEMENTS ASSOCIATED WITH TREATMENT SOLUTIONS |
|---|---|---|---|---|
| 1) distilled $H_2O$ | 10 | 22 | 30 | Elements associated with |
| 2) distilled $H_2O$ | 10 | 22 | 30 | the water soluble and sea water component |
| 3) 1N acetic acid | 10 | 22 | 30 | Elements associated with |
| 4) 1N acetic acid | 10 | 22 | 30 | the acid soluble and carbonate component |
| 5) 1M $Na_2CO_3$ | 10 | 90 | 10 | Elements associated |
| 6) 1M $Na_2CO_3$ | 10 | 120 | 10 | with biogenic silicate component, (diatom and radiolarian tests), and lithogenic component |
| 7) IM $Na_2CO_3$ | 10 | 150 | 10 | Elements associated with |
| 8) IM $Na_2CO_3$ | 10 | 150 | 10 | the robust biogenic silicate component and lithogenic component |
| 9) 98% $HNO_3$ + 2% HF | 5 | 150 | 15 | Elements associated with the remaining resistant and lithogenic component |

Having described the preferred embodiments of the invention, it will now become apparent to one of skill in the art that other embodiments incorporating the disclosed concepts may be used. Therefore, it is not intended to limit the invention to the disclosed embodiments but rather the invention should be limited only by the spirit and scope of the following claims.

What is claimed is:

1. A sequential processing reaction vessel for treatment of solids at high temperatures and pressures comprising:

a pressure resistant, microwave transparent, outer housing, said housing being able to withstand at least 150 psi of internal pressure at temperatures up to at least 150° C.;

a chemically inert, microwave transparent, inner housing, said housing positioned within a cavity formed by said outer housing, said inner housing being resistant to reaction with corrosive liquids at temperatures up to at least 150° C. and internal pressures up to at least 150 psi;

a chemically inert, microwave transparent, filter member, said filter positioned within said inner housing in a substantially horizontal orientation to accommodate placement and retention of a solid sample material, said filter having a pore size which is smaller than a typical particle size of said solid material, said filter permitting retention of said solid material and passage of said corrosive liquids, said filter being resistant to corrosive liquids at temperatures up to at least 150° C. and pressures up to at least 150 psi;

a chemically inert, microwave transparent, top valve, said top valve having an open position for permitting introduction of said corrosive liquids to a reactor volume formed by said inner housing; said top valve having a closed position which provides a leak-proof seal of said vessel at temperatures up to at least 150° C. and pressures up to at least 150 psi; and a chemically inert, microwave transparent, bottom valve, said bottom valve having an open position for permitting removal of said filtered corrosive liquids from said vessel after reactive contact with said solid sample, said bottom valve having a closed position which provides a leak-proof seal of said vessel at temperatures up to at least 150° C. and pressures up to at least 150 psi.

2. The vessel of claim 1, further comprising a chemically inert, microwave transparent filter frit positioned within said inner housing below said membrane filter in a substantially horizontal orientation, said frit having a pore size which is substantially larger than said membrane filter pore size, said frit supporting said filter and permitting passage of said corrosive liquids, said frit being resistant to corrosive liquids at temperatures up to at least 150° C. and pressures up to at least 150 psi.

3. The vessel of claim 1 wherein said filter member comprises a laminated filter assembly comprising a porous, polytetrafluoroethylene membrane filter top layer having a predominately sub-micron pore size, a porous, polytetrafluorethylene filter frit bottom layer having a pore size which is substantially larger than the pore size of said membrane filter, and a non-porous, polytetrafluoroethylene toroidal outer ring for engaging an o-ring seal.

4. The vessel of claim 1 wherein said top and bottom valves further comprise a pressure relief seal which ruptures at excessive vessel pressures.

5. The vessel of claim 1 further comprising auxiliary ports in said top cover to accommodate a temperature sensor and pressure sensor for monitoring vessel reaction conditions.

6. The vessel of claim 1 wherein said outer housing is comprised of a material selected from the group consisting of polyetherimide or glass-filed polyetherimide, said inner housing is comprised of a material selected from the group consisting of polytetrafluoroethylene or perfluoroalkoxy-polytetrafluoroethylene compolymer, said filter is comprised of a material selected from the group consisting of treated hydrophobic polytetrafluoroethylene or hydrophilic polytetrafluoroethylene, and said top and bottom valves are comprised of a material selected from the group consisting of polytetrafluoroethylene or perfluoroalkoxy-polytetrafluoroethylene copolymer.

7. A sequential processing reaction vessel for treatment of solids at high temperatures and pressures comprising:

a chemically inert, microwave transparent, outer housing comprised of a threaded top collar member secured to a top threaded end of a hollow cylindrical exterior jacket, said top collar having a concentric center opening for insertion of an elongated cylindrical top member of a top cover of an inner housing, and a threaded bottom ring member secured to a bottom threaded end of said exterior jacket, said bottom ring having a concentric center opening for insertion of an elongated cylindrical bottom member of a filter holder of said inner housing;

a chemically inert, microwave transparent, said inner housing comprised of said inner housing top cover urged against a top cover o-ring and an interior liner by said top collar member secured to said top end of said exterior jacket, said top cover having a concentric bore extending through said elongated top member from an exterior top end to an interior bottom surface of said top cover, said elongated member top end having a threaded exterior surface, said top cover having a concentric outer shoulder on a top surface for engaging said top collar, said top cover having a beveled outside edge on said cover bottom surface for engaging said top cover o-ring;

a cylindrical interior liner having an outside cylindrical surface mating with an interior cylindrical surface of said exterior jacket, said interior liner top end having an inner shoulder for receiving and engaging said top cover o-ring, said interior liner bottom end having an outer shoulder for engaging said filter holder, said liner outer shoulder having a beveled outside bottom edge, a filter holder o-ring engaged by said beveled edge of said interior liner bottom shoulder, said filter holder urged against said filter holder o-ring and said interior liner by said threaded bottom ring member secured to said bottom end of said exterior jacket, said filter holder top surface having a primary cylindrical cavity for engaging said liner bottom end shoulder, said primary cavity having a bottom surface for supporting said filter and an inside bottom edge for receiving and engaging said filter holder o-ring, said primary cavity bottom surface having a shallow secondary cylindrical cavity for collecting filtered liquids, said secondary cavity bottom surface having a cylindrical bore extending through said elongated bottom member to an externally threaded distal end, said filter holder bottom surface having a concentric external shoulder for engaging said threaded bottom ring;

a chemically inert, microwave transparent, filter member supported by said primary cavity bottom surface, said filter urged against said primary cavity bottom surface, said filter holder o-ring and said inner liner by said threaded bottom ring member secured to said jacket bottom end;

a chemically inert, microwave transparent threaded top valve, said top valve threads engaged with said threaded distal end of said top elongated member, said top valve having an open position for permitting introduction of corrosive liquids to a reactor volume formed by said inner housing; said top valve having a closed position for sealing said vessel at temperatures up to at least 150° C. and pressures up to at least 150 psi; and a chemically inert, microwave transparent, threaded bottom valve, said bottom valve threads engaged with said threaded distal end of said bottom elongated member, said bottom valve having an open position for permitting removal of filtered corrosive liquids from said reactor volume after reactive contact with said solid sample, said bottom valve having a closed position for sealing said vessel at temperatures up to at least 150° C. and pressures up to at least 150 psi.

8. The vessel of claim 7 wherein said filter member comprises a laminated filter assembly comprising a porous, polytetrafluoroethylene membrane filter top layer having a predominately sub-micron pore size, a porous, polytetrafluoroethylene filter frit bottom layer having a pore size which is substantially larger than the pore size of said membrane filter, and a non-porous, polytetrafluoroethylene outer ring for engaging said filter holder o-ring.

9. The vessel of claim 7 further comprising a chemically inert, microwave transparent, filter frit positioned below said filter member and supported by said secondary cavity bottom surface.

10. The vessel of claim 7 wherein said top and bottom valves further comprise a pressure relief seal which ruptures at excessive vessel pressures.

11. The vessel of claim 7 further comprising at least one pair of alignment pins and associated alignment pin bores for alignment and assembly of said interior liner and said filter holder.

12. The vessel of claim 7 further comprising auxiliary ports in said top cover to accommodate a temperature sensor and pressure sensor for monitoring vessel reaction conditions.

13. The vessel of claim 7 wherein said inside surface of said interior liner has a tapered cross section which narrows at the liner bottom.

14. The vessel of claim 7 wherein said outer housing is comprised of a material selected from the group consisting of polyetherimide or glass-filed polyetherimide, said inner housing is comprised of a material selected from the group consisting of polytetrafluoroethylene or perfluoroalkoxy-polytetrafluoroethylene compolymer, said filter is comprised of a material selected from the group consisting of treated hydrophobic polytetrafluoroethylene or hydrophilic polytetrafluoroethylene, and said top and bottom valves are comprised of a material selected from the group consisting of polytetrafluoroethylene or perfluoroalkoxy-polytetrafluoroethylene copolymer.

15. A method for sequential processing and reaction of solids at high temperatures and pressures comprising the steps of:

providing a sequential processing reaction vessel comprised of a pressure resistant, microwave transparent, outer housing, said housing being able to withstand at least 150 psi of internal pressure at temperatures up to at least 150° C.;

a chemically inert, microwave transparent, inner housing, said housing positioned within a cavity formed by said outer housing, said inner housing being resistant to reaction with corrosive liquids at temperatures up to at least 150° C. and internal pressures up to at least 150 psi;

a chemically inert, microwave transparent, filter member, said filter positioned within said inner housing in a substantially horizontal orientation to accommodate placement and retention of a solid sample material, said filter having a pore size which is smaller than a typical particle size of said solid material, said filter permitting retention of said solid material and passage of said corrosive liquids, said filter being resistant to corrosive liquids at temperatures up to at least 150° C. and pressures up to at least 150 psi;

a chemically inert, microwave transparent, top valve, said top valve having an open position for permitting introduction of said corrosive liquids to a reactor volume formed by said inner housing; said top valve having a closed position which provides a leak-proof seal of said vessel at temperatures up to at least 150° C. and pressures up to at least 150 psi; and a chemically inert, microwave transparent, bottom valve, said bottom valve having an open position for permitting removal of said filtered corrosive liquids from said vessel after reactive contact with said solid sample, said bottom valve having a closed position which provides a leak-proof seal of said vessel at temperatures up to at least 150° C. and pressures up to at least 150 psi;

placing a weighed sample on a top surface of said filter;

sealing said inner housing and said bottom valve;

introducing an initial treatment solution through an opening in said top valve;

closing said top valve;

monitoring an internal temperature and pressure of said vessel;

heating said vessel in a microwave oven according to a predetermined temperature and pressure cycle;

cooling said vessel to room temperature;

collecting said initial treatment solution containing extracted analytes from said bottom valve by opening said top valve and said bottom valve;

rinsing said vessel with a solvent to collect residual initial treatment solution and analytes;

closing said bottom valve;

introducing at least one additional treatment solution through said opening in said top valve; and repeating said introducing, monitoring, heating, cooling, collecting, opening, rinsing and closing steps with said at least one additional treatment solution.

16. The method of claim 15 further comprising the step of analyzing the extracted analytes in each of said treatment solutions.

17. The method of claim 15 wherein said collecting step comprises applying vacuum to said bottom valve.

18. The method of claim 15 wherein said collecting step comprises applying pressure to said top valve.

19. The method of claim 15 wherein at least five different treatment solutions are employed.

20. The method of claim 15 wherein at least five different temperature and pressure cycles are employed.

21. A multiple sequential processing reaction vessel system for treatment of solids at high temperatures and pressures comprising:

a plurality of sequential processing reaction vessels comprised of
a pressure resistant, microwave transparent, outer housing, said housing being able to withstand at least 150 psi of internal pressure at temperatures up to at least 150° C.;

a chemically inert, microwave transparent, inner housing, said housing positioned within a cavity formed by said outer housing, said inner housing being resistant to reaction with corrosive liquids at temperatures up to at least 150° C. and internal pressures up to at least 150 psi;

a chemically inert, microwave transparent, filter member, said filter positioned within said inner housing in a substantially horizontal orientation to accommodate placement and retention of a solid sample material, said filter having a pore size which is smaller than a typical particle size of said solid material, said filter permitting retention of said solid material and passage of said corrosive liquids, said filter being resistant to corrosive liquids at temperatures up to at least 150° C. and pressures up to at least 150 psi;

a chemically inert, microwave transparent, top valve, said top valve having an open position for permitting introduction of said corrosive liquids to a reactor volume formed by said inner housing; said top valve having a closed position for sealing said reactor volume at temperatures up to at least 150° C. and pressures up to at least 150 psi; and a chemically inert, microwave transparent, bottom valve, said bottom valve having an open position for permitting removal of said filtered corrosive liquids from said vessel after reactive contact with said solid sample, said bottom valve having a closed position for sealing said reactor volume at temperatures up to at least 150° C. and pressures up to at least 150 psi; and a carousel assembly for supporting said vessels comprised of
a support pedestal;

a bottom plate attached to said support pedestal in a substantially horizontal configuration, said bottom plate configured with a plurality of openings to receive said bottom valve assembly of said vessels and provide access to said bottom valves;

a top plate attached to said support pedestal above said bottom plate in a substantially horizontal configuration, said top plate configured with a plurality of openings to receive said outer housing of said vessels and provide access to said top valves and said vessels;

wherein each of said plurality of outer housing openings in said top plate is vertically aligned and paired with one of said bottom valve assembly openings in said bottom plate to support said plurality of vessels in said carousel assembly.

22. The system of claim 21 further comprising at least one temperature sensor and pressure sensor for monitoring reactions in at least one of said vessels.

23. The system of claim 21 further comprising a rotating pedestal for mounting said carousel assembly with said vessels, said rotating pedestal providing for rotation of said carousel assembly in either a clockwise or counter-clockwise direction to achieve uniform heating of said plurality of vessels when said carousel assembly is placed in an oven.

* * * * *

UNITED STATES PATENT AND TRADEMARK OFFICE
CERTIFICATE OF CORRECTION

PATENT NO. : 6,803,237 B2
DATED : October 12, 2004
INVENTOR(S) : Steven J. Manganini et al.

It is certified that error appears in the above-identified patent and that said Letters Patent is hereby corrected as shown below:

<u>Title page,</u>
Item [75], Inventors, "Terence R. Hammer" should read -- Terence R. Hammar --.

Signed and Sealed this

Third Day of January, 2006

JON W. DUDAS
*Director of the United States Patent and Trademark Office*